United States Patent [19]

Virgilio et al.

[11] 4,182,730
[45] Jan. 8, 1980

[54] PROCESS FOR THE PREPARATION OF SUBSTITUTED DIHYDROCINNAMALDEHYDES VIA NOVEL β-CHLOROCINNAMALDEHYDES

[75] Inventors: Joseph A. Virgilio; Thomas F. Wood, both of Wayne; Emanuel Heilweil, Fairfield; Harold A. Brandman, Glen Ridge, all of N.J.

[73] Assignee: Givaudan Corporation, Clifton, N.J.

[21] Appl. No.: 854,927

[22] Filed: Nov. 25, 1977

[51] Int. Cl.$^2$ .................................................. C07C 45/00
[52] U.S. Cl. .................................. 260/599; 260/600 R
[58] Field of Search ................................ 260/599, 600

[56] References Cited

U.S. PATENT DOCUMENTS 4,125,563  11/1978  Boschan .......................... 260/599 X

OTHER PUBLICATIONS

Arnold et al., Collection Czechoslov. Chem. Commun., vol. 24, (1959), 2385–2392.
Berends et al., Perfumery and Essential Oil Record, vol. 58, (1967), 372–378.

*Primary Examiner*—Bernard Helfin
*Attorney, Agent, or Firm*—Robert F. Tavares; Thomas Cifelli, Jr.

[57] ABSTRACT

A novel process for producing a substituted α-alkyl-dihydrocinnamaldehydes from the corresponding alkyl-phenone via a novel α-alkyl-β-chlorocinnamaldehyde.

7 Claims, No Drawings

PROCESS FOR THE PREPARATION OF SUBSTITUTED DIHYDROCINNAMALDEHYDES VIA NOVEL β-CHLOROCINNAMALDEHYDES

BACKGROUND OF THE INVENTION

A number of substituted α-alkyldihydrocinnamaldehydes are known odoriferous substances. W. Berends and L. M. v.d. Linde, Perfumery and Essential Oil Record, 58, 372 (1967). Some of these compounds, particulary p-isopropyl-α-methyldihydrocinnamaldehyde and p-t-butyl-α-methyldihydrocinnamaldehyde, are among the principal aromatic compounds used in the industry.

These compounds are usually made by the multistep process shown below which involves a condensation reaction of an aromatic aldehyde with the α-methylene of an aliphatic aldehyde

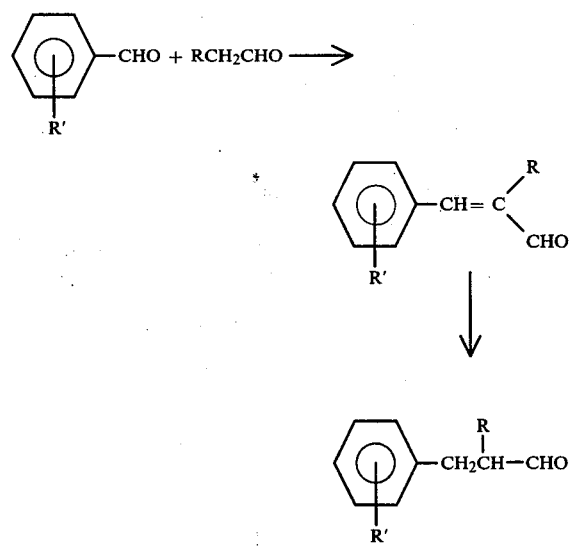

Other methods of synthesis are reviewed in the Berends article above. (R and R' are suitable substituents as defined herein.)

The success of this multistep process necessarily depends on the availability of the appropriate corresponding benzaldehyde and the ability to minimize side reactions such as self condensation of the aliphatic aldehyde and/or the Cannizzaro reaction.

SUMMARY OF THE INVENTION

This invention provides a novel and commercially viable method for converting an aryl alkyl ketone to the desired α-alkyldihydrocinnamaldehydes in a two step process which involves the novel intermediate α-alkyl-β-chlorocinnamaldehydes as shown below.

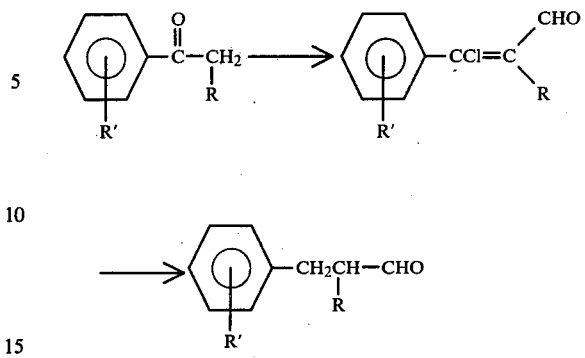

The first step is accomplished via the Vilsmeier reagent and the second via a catalytic hydrogenation in the presence of base. The hydrogenation reduces the double bond and removes the chlorine in the same reaction while leaving the carbonyl group intact.

DESCRIPTION OF THE PREFERRED EMBODIMENTS

One of the most attractive aspects of this process, is that it provides for the conversion of readily available substituted aryl alkyl ketones to the corresponding α-alkyldihydrocinnamaldehydes. Most of the substituted aryl alkyl ketones are commercially available or can be easily prepared via a Friedel Crafts reaction between the appropriate substituted benzene and the aliphatic acid or acid chloride.

The substituted aryl alkyl ketones are then reacted with the Vilsmeier reagent to form the corresponding α-alkyl-β-chlorocinnamaldehydes. The Vilsmeier reagent is a well known reagent which, in its broadest sense, is the product that results when a disubstituted amide is reacted with an acid chloride. Derek Burn, Alkylation with the Vilsmeier Reagent, Chemistry and Industry, 1973, 870. Vilsmeier reagents used for formylation are most commonly prepared by reacting dimethyl formamide or methylformanilide with phosphoryl chloride or phosgene.

It is preferred to prepare the Vilsmeier reagent with dimethylformamide and phosphorous oxychloride. While the reagent may be prepared in a reaction inert solvent, such as any suitable Friedel Crafts type solvent, it is preferred to use excess dimethylformamide as solvent.

Only one equivalent of dimethylformamide per equivalent of phosphorous oxychloride is required. Usually, however, the dimethylformamide is used as solvent and an extra equivalent or two is used for this purpose. A larger excess is not necessary, but may be used without detrimental effect.

The formation of the Vilsmeier reagent is exothermic and it is preferred to add the phosphorous oxychloride to the dimethylformamide at such a rate as to keep the temperature below 25° C. with external cooling.

Once the Vilsmeier reagent is formed, the ketone is added dropwise. While the reaction may be run anywhere from below 0° C. to above 110° C., it is preferred to add the ketone to the Vilsmeier reagent at a temperature between 50° C. and 100° C., a temperature of 60° to 85° being especially preferred.

The reaction time is dependent upon the temperature and the reactants used. It can vary from 30 minutes to 24 hours. Most reactions run under preferred conditions are complete in about three to twelve hours.

The β-chloroaldehydes are isolated by treating the reaction mixture with a suitable aqueous base (sodium hydroxide, sodium acetate, potassium carbonate and the like) in an amount sufficient to hydrolyse the Vilsmeier intermediate, extracting the product with a suitable organic solvent, removing the solvent by distillation and purifying the product by vacuum distillation.

The substituted α-alkyl-β-chlorocinnamaldehydes of this invention are precursors to odorant materials. It is therefore preferred that R' be hydrogen, methoxy or an alkyl group of from one to seven carbons, that R be an alkyl group of from one to eight carbons and that the number of carbon atoms in the sum of R and R' be no less than two and no greater than eight. It is also understood that R' can represent one or more alkyl groups on the aromatic ring.

The novel β-chlorocinnamaldehydes of this invention are illustrated by, but not limited to the following:
β-Chloro-4-methoxy-α-methylcinnamaldehyde
β-Chloro-4-ethyl-α-methylcinnamaldehyde
β-Chloro-4,α-dimethylcinnamaldehyde
β-Chloro-4-isopropyl-α-methylcinnamaldehyde
4-tert-Butyl-β-chloro-α-methylcinnamaldehyde
β-Chloro-2,4-α-trimethylcinnamaldehyde
β-Chloro-2,4,5-α-tetramethylcinnamaldehyde
β-Chloro-4-n-heptyl-α-methylcinnamaldehyde
β-Chloro-α-n-octylcinnamaldehyde The β-chlorocinnamaldehydes of this invention can be converted to the desired dihydrocinnamaldehydes in a single step by a catalytic hydrogenation which hydrogenates the olefinic bond and removes the chlorine while leaving the aldehyde group intact.

The preferred method utilizes palladium as the hydrogenation catalyst, a base sufficient to neutralize the hydrochloric acid formed and a small amount of water. The preferred conditions for carrying out the hydrogenation are those described in U.S. Pat. No. 3,860,657 (which describes the hydrogenation of citral to citronellal) with the exception that enough base is utilized to neutralize the hydrchloric acid that is formed.

While any palladium catalyst can be used it is preferred to use the commercially available forms of palladium deposited on a carrier such as carbon or alumina. It is preferred to utilize 0.2 to 5 grams of 5 percent palladium on carbon or alumina per 100 grams of α-alkyl-β-chlorocinnamaldehyde to be hydrogenated.

The base may be any selected from the group consisting of alkali metal hydroxides, alkaline earth metal hydroxides, salts of strong bases with weak acids, and amines. Preferred are the readily available alkali metal hydroxides, alkali metal carbonates and tertiary amines. Especially preferred are the commonly used sodium or potassium carbonate, sodium or potassium hydroxide, and triethyl amine. The amount of base preferred is enough to neutralize the hydrochloric acid formed plus a slight excess. When carbonates are used it is preferred to use at least a mole of carbonates per mole of α-alkyl-β-chlorocinnamaldehyde so that the by-product will be bicarbonate rather than carbon dioxide. The amount of base especially preferred is 1.01 to 1.1 moles per mole of α-alkyl-β-chlorocinnamaldehyde to be reduced.

It is preferred to use an amount of water sufficient to slurry the inorganic bases. An excess of water is not detrimental.

When an organic base is used the amount of water need only be in excess of 0.3 grams of water per 100 grams of the α-alkyl-β-chlorocinnamaldehyde to be reduced. Especially preferred would be about one to two grams of water per 100 grams of starting material.

The temperature and pressure are not critical. The temperature can range from 5° C. to 150° C. and the pressure can range from below one atmosphere to above 40 atmospheres. Especially preferred is a pressure in the range of about 3 atmospheres to about 5 atmospheres.

Upon completion of the hydrogenation the catalyst is removed by filtration and the product purified by distillation.

A number of examples are provided herein, they are intended to illustrate the preferred embodiments of the invention and should not be construded as limiting. They are intended to embrace any equivalents or obvious extensions which are known or should be known to a person skilled in the art. All temperatures are in degrees centigrade.

EXAMPLE I 4-tert-Butyl-β-chloro-α-methylcinnamaldehyde

Phosphorous oxychloride (462 g) was added to 400 g of dimethylformamide (DMF) at such a rate as to maintain the temperature below 25° by ice bath cooling. After stirring for 30 min, 4-tert-butylpropiophenone (190 g) was added dropwise to the mixture at 70°–80°. The solution was heated at 70°–80° for 5 hrs. The reaction was cooled and 720 g of 30% sodium hydroxide solution was added so that the temperature was maintained below 70° by ice bath cooling. The solution was stirred at 60°–70° for 30 min. Water (500 g) was added and the mixture extracted with 3×400 ml of ethylene dichloride. The combined extracts were concentrated and distilled to yield 227.2 g (96%) of product, bp 122° (1.0 mm).

Analysis calcd for $C_{14}H_{17}ClO$: C, 71.02; H, 7.22; Cl, 15.00. Found: C, 71.04; H, 7.52; Cl, 14.78.

EXAMPLE II

β-Chloro-4-isopropyl-α-methylcinnamaldehyde

4-Isopropylpropiophenone (176.2 g) was reacted in the same manner as Example I to yield 213.6 g (96%) of the desired product, bp 114° (1.0 mm).

Analysis calcd for $C_{13}H_{15}ClO$: C, 70.09; H, 6.78; Cl, 15.94. Found: C, 70.26; H, 6.86; Cl, 15.66.

EXAMPLE III

β-Chloro-4-methoxy-α-methylcinnamaldehyde $POCl_3$ (185 g) was added to 185 g of DMF at such a rate as to maintain the temperature below 25° by ice bath cooling. After stirring for 30 min, 4-methoxypropiophenone (82.1 g) was added dropwise to the mixture at 60°–65°. The reaction was maintained at 80°–90° for 8 hrs. Toluene (174 g) was added and 1-liter of a saturated sodium acetate solution was added so that a temperature of 65° was maintained by ice bath cooling. After heating at 70°–80° for 2 hrs. the organic phase was separated and washed with 300 ml of 5% $NaHCO_3$. Distillation yielded 90 g (86%) of the desired product, bp 130° (1.0 mm).

Analysis calcd for $C_{11}H_{11}ClO_2$: C, 62.71; H, 5.26; Cl, 16.83. Found: C, 62.62; H, 5.41; Cl, 17.07.

EXAMPLE IV

β-Chloro-4-ethyl-α-methylcinnamaldehyde

4-Ethylpropiophenone (81.1 g) was reacted in the same manner as Example III to yield 90.2 g (86%) of the desired product, bp 118° (1.3 mm). NMR spectral data were consistent with the assigned structure.

EXAMPLE V

β-Chloro-4,α-dimethylcinnamaldehyde

4-Methylpropiophenone (74.1 g) was reacted in the same manner as Example III to yield 85.2 g (88%) of the desired product, bp 98° (1.0 mm). NMR spectral data were consistent with the assigned structure.

EXAMPLE VI

β-Chloro-2,4,α-trimethylcinnamaldehyde 2,4-Dimethylpropiophenone 81.1 g was reacted in the same manner as Example III to yield 90.6 g (86.9%) of the desired product, bp 110° (1.0 mm).

Analysis calcd for $C_{12}H_{13}ClO$: C, 69.06; H, 6.28; Cl, 16.99. Found: C, 68.89; H, 6.43; Cl, 17.12.

EXAMPLE VII

β-Chloro-2,4,5,α-tetramethylcinnamaldehyde 2,4,5-Trimethylpropiophenone 88.1 g was reacted in the same manner as Example III to yield 92.6 g (83.2%) of the desired product, bp 115° (1.3 mm).

Analysis calcd for $C_{13}H_{15}ClO$: C, 70.10; H, 6.79; Cl, 15.92. Found: C, 70.08; H, 6.71; Cl, 15.68.

EXAMPLE VIII

β-Chloro-4-n-heptyl-α-methylcinnamaldehyde 4-n-Heptylpropiophenone 116.2 g was reacted in the same manner as Example III to yield 127.6 g (91.5%) of the desired product, bp 165° (1.2 mm).

Analysis calcd for $C_{17}H_{13}ClO$: C, 73.23; H, 8.31; Cl, 12.72. Found: C, 73.29; H, 8.24; Cl, 12.85.

EXAMPLE IX

β-Chloro-α-n-octylcinnamaldehyde

Decanophenone 116.2 g was reacted in the same manner as Example III to yield 103.2 g (74%) of the desired product, bp 159° (1.3 mm).

Analysis calcd for $C_{17}H_{23}ClO$: C, 73.23; H, 8.31; Cl, 12.72. Found: C, 73.42; H, 8.57; Cl, 12.76.

EXAMPLE X 4-tert-Butyl-α-methyldihydrocinnamaldehyde 4-tert-Butyl-β-chloro-α-methylcinnamaldehyde (71 g), 1.0 g of 5% Pd/C, 40 g of 30% sodium hydroxide solution, 40 g of water and 32 g of methanol were placed in a Parr apparatus and hydrogenated at 20–50 psi until the theoretical amount of hydrogen had been absorbed (about 3½ hrs.). The solution was filtered and the aqueous phase extracted with 100 g of ethylene dichloride. The solution was distilled to yield 53.9 g (76%) of the desired product, bp 100° (1.0 mm).

EXAMPLES XI THROUGH XVIII

The procedure of Example X was repeated using the various β-chloroaldehydes described in Table I.

TABLE I

| Example | β-Chloroaldehyde | Product after hydrogenation | bp(mm) |
| --- | --- | --- | --- |
| 11 | (i-Pr)C₆H₄—CCl=C(CH₃)(CHO) | (i-Pr)C₆H₄—CH₂CHCH₃CHO | 140° (1.0) |
| 12 | MeO—C₆H₄—CCl=C(CH₃)(CHO) | MeO—C₆H₄—CH₂CHCH₃CHO | 118° (1.5) |
| 13 | (alkyl)C₆H₄—CCl=C(CH₃)(CHO) | (alkyl)C₆H₄—CH₂CHCH₃CHO | 88° (0.9) |
| 14 | C₆H₅—CCl=C(CH₃)(CHO) | C₆H₅—CH₂CHCH₃CHO | 60° (0.1) |
| 15 | (alkyl)C₆H₄—CCl=C(CH₃)(CHO) | (alkyl)C₆H₄—CH₂CHCH₃CHO | 92° (1.0) |
| 16 | (alkyl)C₆H₄—CCl=C(CH₃)(CHO) | (alkyl)C₆H₄—CH₂CHCH₃CHO | 120° (2.0) |
| 17 | CH₃(CH₂)₆—C₆H₄—CCl=C(CH₃)(CHO) | CH₃(CH₂)₆—C₆H₄—CH₂CHCH₃CHO | 158° (1.2) |

TABLE I-continued

| Example | β-Chloroaldehyde | Product after hydrogenation | bp(mm) |
|---|---|---|---|
| 18 | phenyl-CCl=C((CH₂)₇CH₃)(CHO) | phenyl-CH₂CH((CH₂)₇CH₃)(CHO) | 148° (1.0) |

We claim:

1. A process for preparing a substituted α-alkyldihydrocinnamaldehyde of the formula

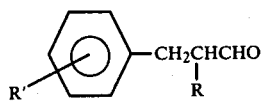

wherein:
R' represents hydrogen, methoxy or one or more alkyl groups wherein the number of carbon atoms in R' does not exceed seven;
R is an alkyl group of from one to eight carbons; and the number of carbon atoms in the sum of R and R' is not less than two and is not greater than eight; which comprises reacting a ketone of the formula

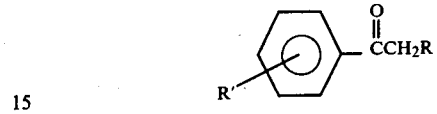

with a Vilsmeier reagent, prepared by reacting dimethylformamide with phosphorous oxychloride or phosgene, to provide the intermediate α-alkyl-β-chlorocinnamaldehyde

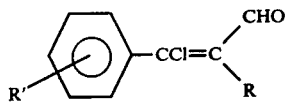

and then hydrogenating to the α-alkyldihydrocinnamaldehyde in the presence of a catalyst consisting essentially of palladium, water and a base.

2. The process of claim 1 wherein R is methyl.
3. The process of claim 2 wherein R' is in the para position.
4. The process of claim 3 wherein R' is an alkyl group of from one to seven carbon atoms.
5. The process of claim 3 wherein R' is isopropyl.
6. The process of claim 3 wherein R' is t-butyl.
7. The process of claim 3 wherein R' is methoxy.

* * * * *